US011085978B2

(12) United States Patent
Connell et al.

(10) Patent No.: US 11,085,978 B2
(45) Date of Patent: Aug. 10, 2021

(54) ORTHOGONAL ELEMENT DECOUPLING FOR MOVEABLE COIL ARRAYS IN MRI

(71) Applicant: SYNAPTIVE MEDICAL INC., Toronto (CA)

(72) Inventors: Ian Robert Oliphant Connell, Toronto (CA); Gilbert Thevathasan, Toronto (CA); William Wai-Leung Lau, Toronto (CA); Alexander Gyles Panther, Toronto (CA)

(73) Assignee: Synaptive Medical Inc., Toronto (CA)

( * ) Notice: Subject to any disclaimer, the term of this patent is extended or adjusted under 35 U.S.C. 154(b) by 12 days.

(21) Appl. No.: 16/435,324

(22) Filed: Jun. 7, 2019

(65) Prior Publication Data

US 2020/0386834 A1   Dec. 10, 2020

(51) Int. Cl.
*G01R 33/34* (2006.01)
*A61B 5/055* (2006.01)
*G01R 33/341* (2006.01)

(52) U.S. Cl.
CPC ........ *G01R 33/34084* (2013.01); *A61B 5/055* (2013.01); *A61B 2560/04* (2013.01); *G01R 33/341* (2013.01)

(58) Field of Classification Search
USPC ........................................ 324/307, 318, 322
See application file for complete search history.

(56) References Cited

U.S. PATENT DOCUMENTS

| 5,256,971 | A | 10/1993 | Boskamp |
| 6,639,406 | B1 | 10/2003 | Boskamp et al. |
| 2004/0124840 | A1 | 7/2004 | Reykowski |
| 2007/0270683 | A1 | 11/2007 | Meloy |
| 2008/0306377 | A1* | 12/2008 | Piron ............... A61B 90/10 600/422 |
| 2013/0131498 | A1 | 5/2013 | Taracila et al. |
| 2013/0317346 | A1 | 11/2013 | Alagappan et al. |
| 2015/0057528 | A1 | 2/2015 | Driemel |
| 2018/0356477 | A1* | 12/2018 | Lau .................. G01R 33/34084 |

FOREIGN PATENT DOCUMENTS

| WO | WO 2002/39135 | 5/2002 |
| WO | WO 2017130025 | 8/2017 |

OTHER PUBLICATIONS

GB Examination Report issued by the Intellectual Property Office of the UK in relation to GB Application No. GB2008638.5, dated Dec. 9, 2020, 2 pages.

* cited by examiner

*Primary Examiner* — Vincent Q Nguyen
(74) *Attorney, Agent, or Firm* — Fish & Richardson P.C.

(57) ABSTRACT

A head coil assembly includes a housing with a lower portion, an upper portion, a left portion, and a right portion, wherein each portion includes two or more radio-frequency (RF) coils, wherein the portions are sized and shaped to adjustably conform to a curvature of the subject's head for magnetic resonance (MR) imaging of the subject's head placed inside the housing, wherein the portions are operable to transition from an open position where the portions are sufficiently apart from each other to a closed position where the portions are adjusted to tighten a wrap around the subject's head along the curvature, and wherein the two or more RF coils in each portion are disposed in such manner that when the portions are operated to transition from the open position to the closed position, the RF coils of each portion remain decoupled to each other even along edges of each portion.

15 Claims, 10 Drawing Sheets

ORTHOGONAL ELEMENT DECOUPLING FOR MOVEABLE COIL ARRAYS IN MRI

BACKGROUND

The present disclosure relates to magnetic resonance imaging.

SUMMARY

In one aspect, some implementations provide a head coil assembly for performing magnetic resonance (MR) imaging of a subject. The method includes: a housing comprising a lower portion, an upper portion, a left portion, and a right portion, wherein each portion comprises two or more radio-frequency (RF) coils for performing magnetic resonance (MR) imaging of the subject's head placed inside the housing, wherein the portions are sized and shaped to adjustably conform to a curvature of the subject's head such that the portions are operable to transition from an open position to a closed position, wherein when the portions are in the open position, the portions are sufficiently apart from each other to accommodate the subject's head being slid into the housing, wherein when the portions are in the closed position, the portions are adjusted to more closely wrap around the subject's head along the curvature, and wherein the two or more RF coils in each portion are disposed in such manner that when the portions are operated to transition from the open position to the closed position, the RF coils of each portion remain decoupled to each other even along edges of each portion.

Implementations may include one or more of the following features.

The head coil assembly may further include: a tongue sized and shaped to hold the subject's head when the subject is lying on a transporter, the tongue configured to be dockable with the lower portion to slide the subject's head into the housing when the housing is in the open position.

The housing may include butterfly-loop decoupling pairs disposed along edges of each individual portion. Each butterfly-loop decoupling pair comprises a loop element and a butterfly element, wherein the loop element is located on a first portion while the butterfly element is located on a second portion, and wherein the first portion and the second portion are neighboring portions from among the lower portion, the upper portion, the left portion, and the right portion. Each butterfly-loop decoupling pair may be configured to receive, in response to one or more radio frequency (RF) excitation pulses directed at the subject's head placed inside the head coil assembly, first MR signals at the loop element and second MR signals at the butterfly element.

Each butterfly-loop decoupling pair may not configured as a quadrature pair such that the first MR signals received at the loop element and the second MR signals received at the butterfly element maintain no fixed phase shift, and wherein the first and second MR signals are digitized and then digitally recombined when an MR image is reconstructed.

The first MR signals received at the loop element and the second MR signals received at the butterfly element are analog signals and combined after digitization The housing may include loop-loop decoupling pairs disposed along edges of each individual portion. Each loop-loop decoupling pair includes a first loop element located on a first portion and a second loop element located on a second portion, wherein the first portion and the second portion are neighboring portions from among the lower portion, the upper portion, the left portion, and the right portion, and wherein the loop-loop decoupling pair remains orthogonally disposed when the portions transition from the open position to the closed position or vice versa. Each loop-loop decoupling pair may be configured to receive, in response to one or more radio frequency (RF) excitation pulses directed at the subject's head placed inside the head coil assembly, first MR signals received at the loop element and second MR signals received at the butterfly element, and wherein the first and second MR signals are digitized and then digitally recombined when an MR image is reconstructed. Each loop-loop decoupling pair is configured such that the first MR signals received at the first loop element and the second MR signals received at the second loop element are not fixed in phase shifts relative to each other.

In another aspect, some implementations provide a method for operating a head coil assembly on a magnetic resonance imaging (MRI) system, the method including: configuring a housing of the head coil assembly in an open position, wherein the housing comprises a lower portion, an upper portion, a left portion, a right portion, and a tongue, wherein each portion comprises two or more radio-frequency (RF) coils, wherein the RF coils of each portion are decoupled to coils from other portions, and wherein each portion is sized and shaped to adjustably conform to a curvature of the subject's head; docking the tongue with the lower portion by moving a transporter carrying the subject to the MRI system; reconfiguring the housing of the head coil assembly from the open position wherein the portions are sufficiently apart from each other to accommodate the subject's head being slid into the housing to a closed position wherein the portions are adjusted to more closely wrap around the subject's head along the curvature, wherein the RF coils of each portion remain decoupled to RF coils from other portions even along edges of each portion; and sliding the housing into the MRI system.

Implementations may include one or more of the following features.

The housing may include butterfly-loop decoupling pairs disposed along edges of each individual portion. The method may further include: operating the MRI system to receive, in response to one or more radio frequency (RF) excitation pulses directed at the subject's head placed inside the head coil assembly, first MR signals at the loop element and second MR signals at the butterfly element. The first MR signals received at the loop element and the second MR signals received at the butterfly element may maintain no fixed phase shift. The first and second MR signals may be digitized and then digitally recombined when an MR image is reconstructed. The first MR signals received at the loop element and the second MR signals received at the butterfly element may be analog signals and combined after digitization.

The housing may include loop-loop decoupling pairs disposed along edges of each individual portion. Each loop-loop decoupling pair includes a first loop element located on a first portion and a second loop element located on a second portion, wherein the first portion and the second portion are neighboring portions from among the lower portion, the upper portion, the left portion, and the right portion, and wherein the loop-loop decoupling pair remains orthogonally disposed when the portions transition from the open position to the closed position or vice versa. The method may further include: operating the MRI system to receive, in response to one or more radio frequency (RF) excitation pulses directed at the subject's head placed inside the head coil assembly, first MR signals received at the loop element and second MR signals received at the butterfly element, and wherein the first and second MR signals are digitized and then digitally recombined when an MR image is reconstructed. The first MR signals received at the first loop element and the second MR signals received at the second loop element may not be fixed in phase shifts relative to each other.

The details of one or more aspects of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference symbols in the various drawings indicate like elements.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Magnetic resonance (MR) imaging employs radio frequency (RF) coil arrays. A RF coil array includes multiple resonating antennas disposed in a judicious manner for imaging a particular region. While RF coil arrays are predominately built and optimized for specific imaging targets, these coil arrays do abide by the general objectives of maximizing efficiency during transmission of an RF signal and maximizing signal to noise ratio (SNR) of the received MR signal during reception. The transmission efficiency and the reception SNR are balanced in various trade-offs to combat a common electromagnetic phenomenon known as electromagnetic coupling. In some instances, RF coils are built on fixed, rigid assemblies such that the electromagnetic coupling can be mitigated using critical element overlap and low-input impedance preamplifiers. In contrast, conformable RF coils fit over a curvature may not incorporate critical element overlap and preamplifiers. In one illustration, when the conformable RF coils are to be placed in close proximity to the region being imaged, space limitations may not be conducive to introducing an element overlap or including a preamplifier. Moreover, when the conformable array is being re-configured, the overlap may not be maintained as the conformable array transitions from one configuration to another configuration.

Instead, examples disclosed in the present disclosure provides systems and methods for electromagnetically isolating the individual moving parts of the RF array from one another to reduce the coupling in the array. Moreover, the disclosed systems and methods may maintain the decoupling status when the conformable array is being reconfigured.

Figure 1:
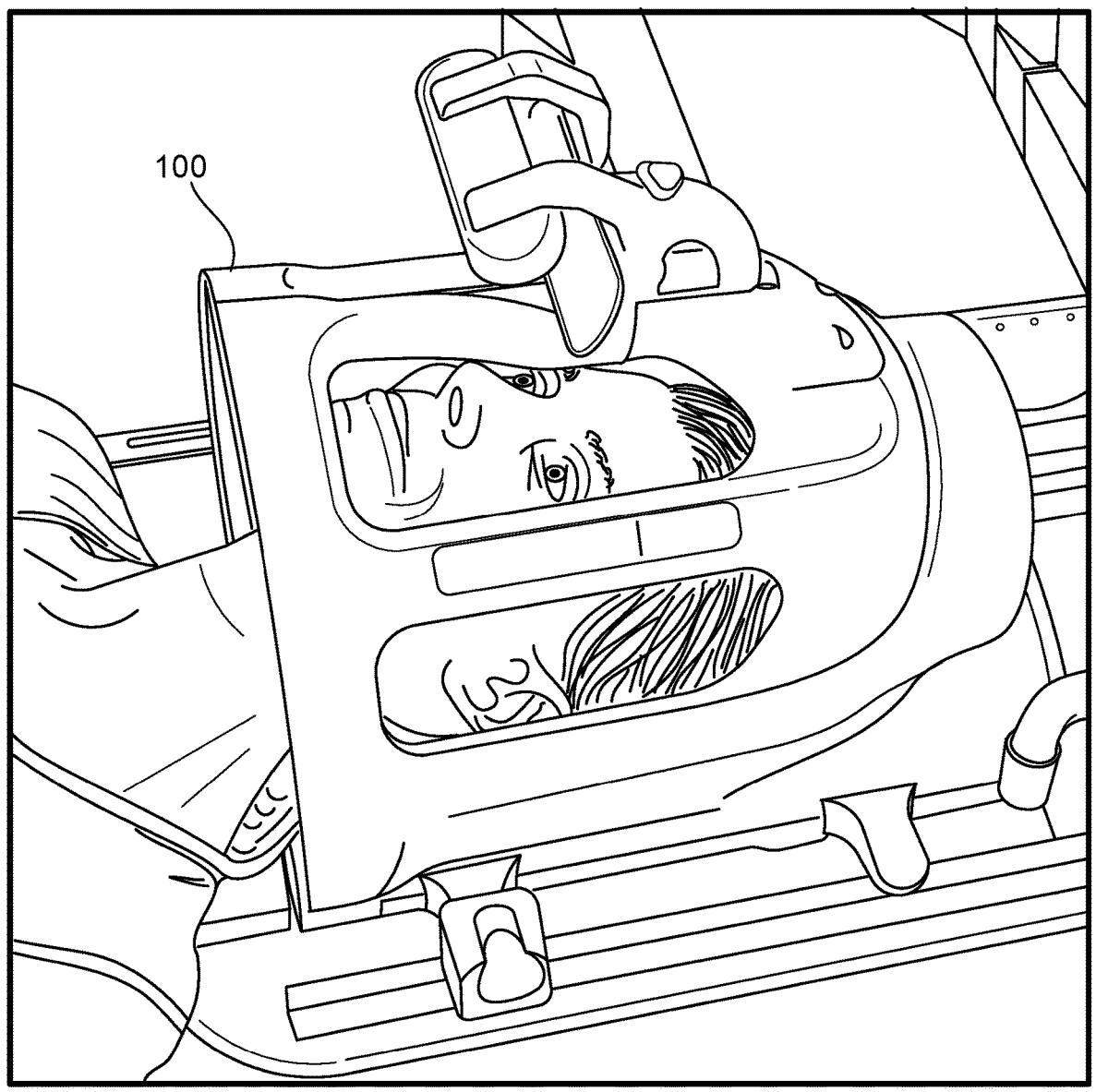
FIG. 1 is a diagram illustrating, in a perspective view, an MRI "head coil" or an MRI "brain coil" having a birdcage configuration.

Referring to FIG. 1, this diagram illustrates an MRI "head coil" or an MRI "brain coil" 100 that typically has a birdcage configuration, in accordance with the related art. These related art head coils are cumbersome and also cause various types of physical and emotional distress in a subject, such as a patient, including claustrophobia. Referring physicians, radiologists, and MRI technologists currently attempt to manage affected patients by understanding the etiology of the problem and attempting an appropriate maneuver or an appropriate intervention to counter-act the condition.

Figure 2A:
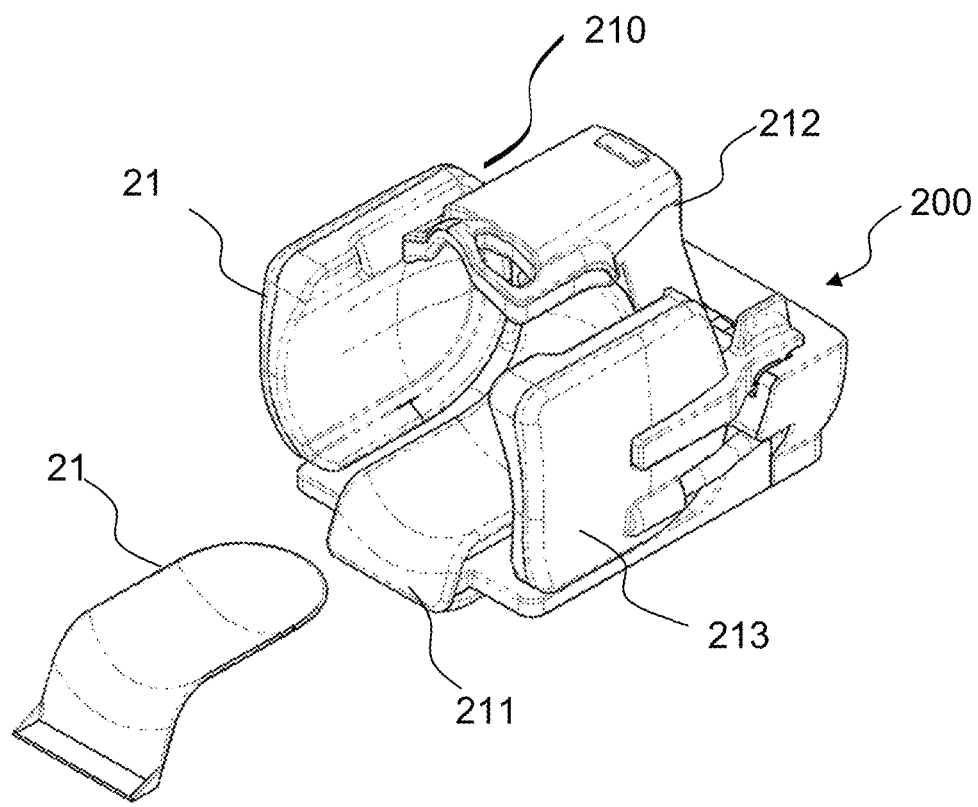
FIGS. 2A to 2D illustrate various views of a head coil system for enhancing and/or optimizing MRI in an open position, in accordance with an example of the present disclosure.
Figure 2B:
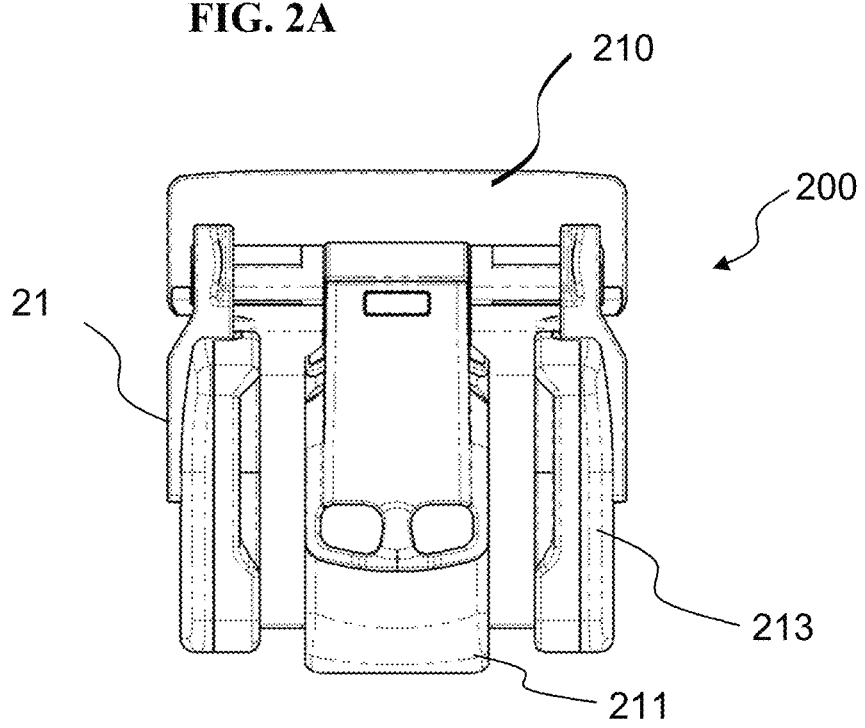
Figure 2C:
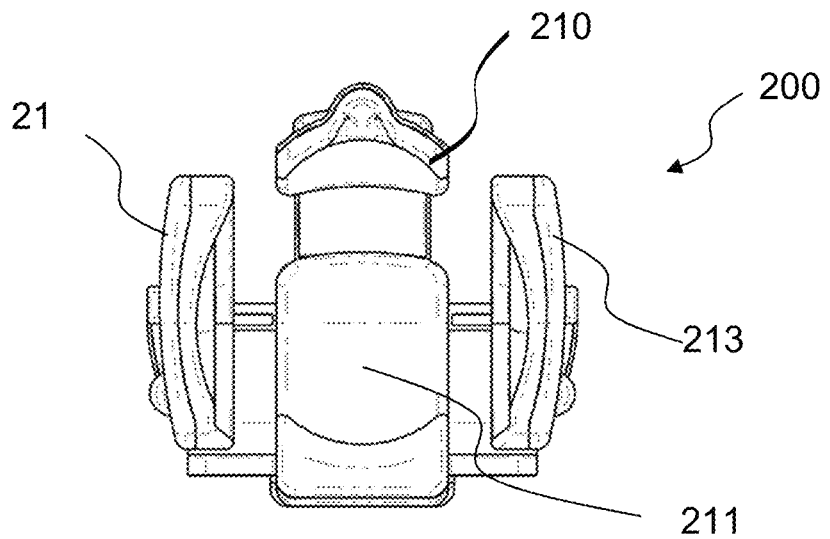
Figure 2D:
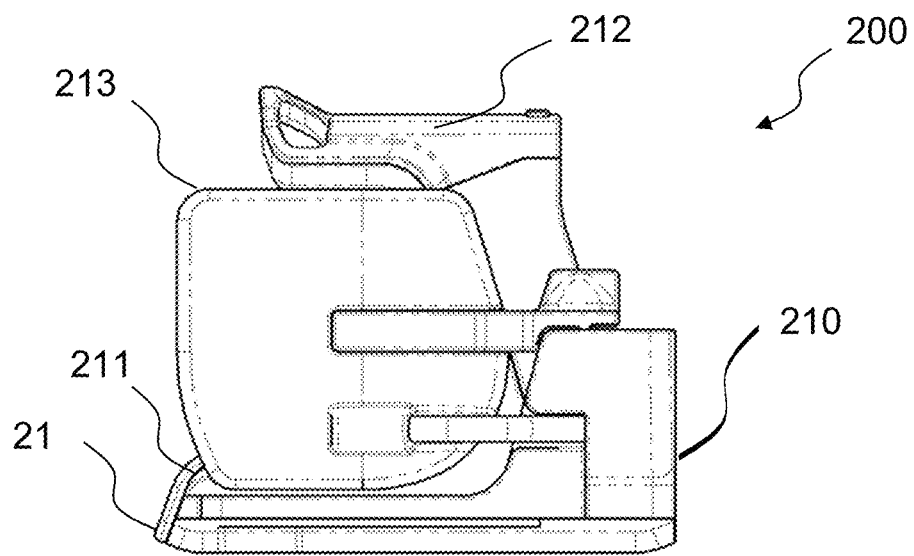

Referring to FIGS. 2A to 2D, the diagrams illustrate a head coil system 200 for enhancing and/or optimizing MRI in an open position, in accordance with an example of the present disclosure. The optionally adjustable head coil system 200 for enhancing and/or optimizing magnetic resonance imaging, comprises: a housing 210, the housing 210 comprising at least one portion, the at least one portion comprising portions, such as a lower portion 211, an upper portion 212, and opposing side portions 213A and 213B, each at least one portion optionally in movable relation to any other portion for facilitating adjustability, each at least one portion configured to accommodate at least one radio-frequency coil 520 (see e.g., FIGS. 5A and 5B), and the upper portion 212 and the lower portion 211 each optionally configured to overlap and engage the opposing side portions 213A and 213B for facilitating decoupling the at least one radio-frequency coil 20; and a tongue portion 214 optionally in movable relation to any other at least one portion for facilitating at least one of adjustability and dockability, engageable with the lower portion 211, and fixably couple-able with a transporter 400 (see e.g., FIGS. 4A to 4B). At least one of each at least one portion, such as a lower portion 211, an upper portion 212, and opposing side portions 213A and 213B, and the tongue portion 214 is configured to be spaced apart in relation to another at least one portion, such as a lower portion 211, an upper portion 212, and opposing side portions 213A and 213B, in an open position. In particular, FIG. 2A represents a perspective view, FIG. 2B is a bottom view, FIG. 2C is a top view, while FIG. 2D is a side view.

Referring to FIGS. 3A to 3D, these diagram illustrate a head coil system 200 for enhancing and/or optimizing MRI in a closed position, in accordance with an example of the present disclosure. The head coil system 200 is adjustable. The optionally adjustable head coil system 200 for enhancing and/or optimizing magnetic resonance imaging, comprises: a housing 210, the housing 210 comprising at least one portion, the at least one portion comprising portions, such as a lower portion 211, an upper portion 212, and opposing side portions 213A and 213B, each at least one portion optionally in movable relation to any other at least one portion for facilitating adjustability, each at least one portion configured to accommodate at least one radio-frequency coil 520 (see e.g., FIGS. 5A to 5B), the upper portion 212 and the lower portion 211 each optionally configured to overlap and engage the opposing side portions 213A and 213B for facilitating decoupling the at least one radio-frequency coil 20, the lower portion 211 optionally engageable with the opposing side portions 213A and 213B; and a tongue portion 214 optionally in movable relation to any other portion for facilitating at least one of adjustability and dockability, engageable with the lower portion 211, and fixably couple-able with a transporter 400 (as will be illustrated in FIGS. 4A to 4B).

Figure 3A:
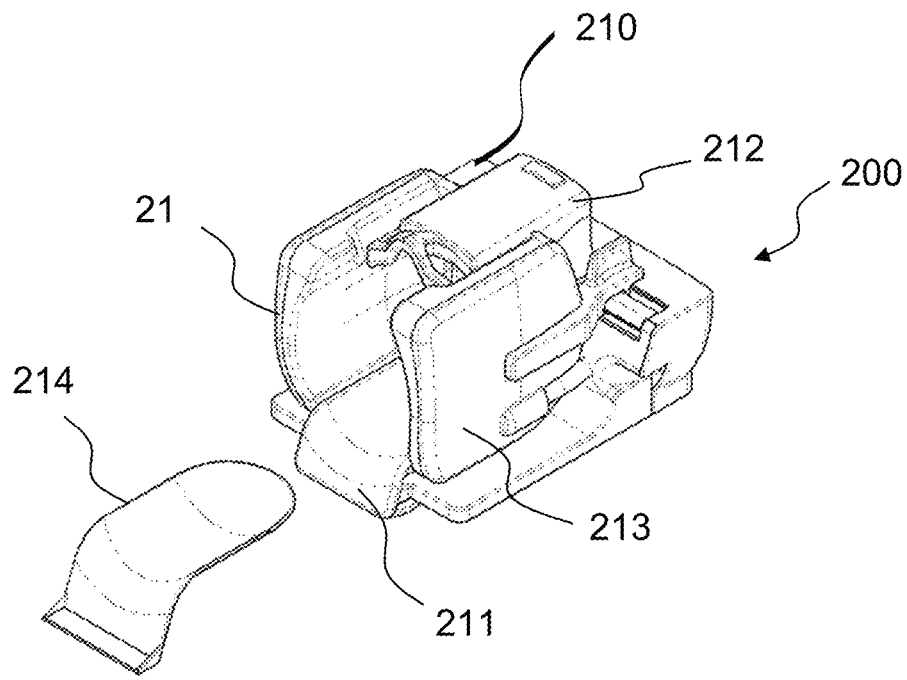
FIGS. 3A to 3D illustrate various views of a head coil system for enhancing and/or optimizing MRI in a closed position, in accordance with an example of the present disclosure.
Figure 3B:
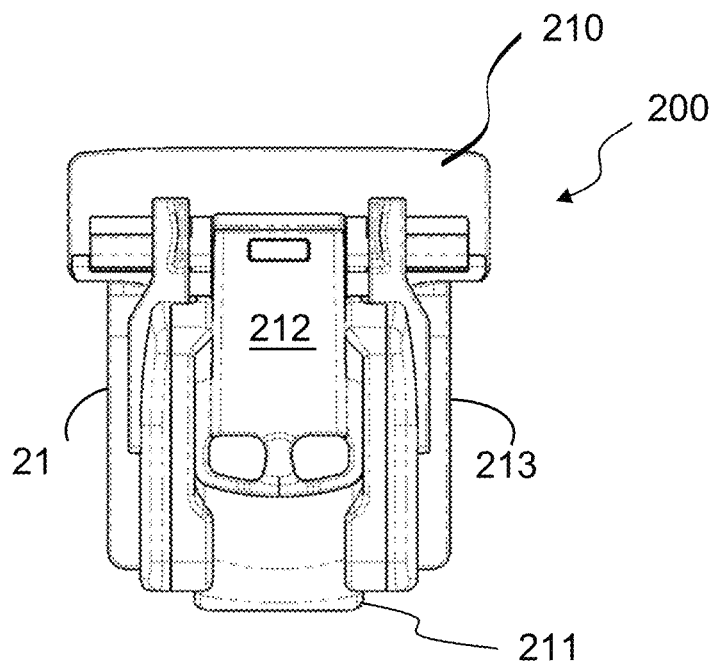
Figure 3C:
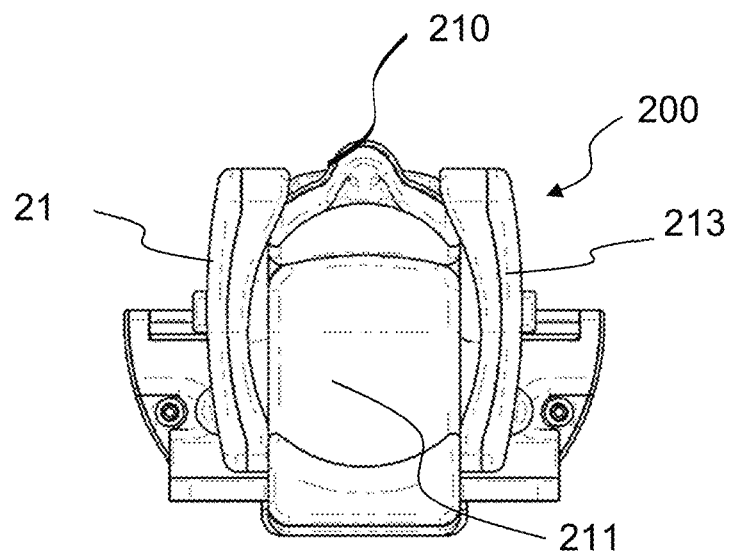
Figure 3D:
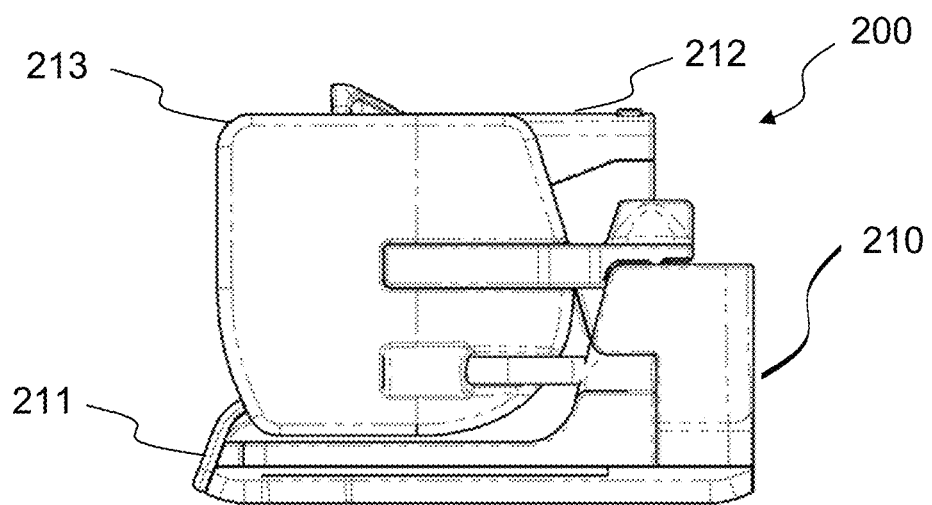

As illustrated in FIGS. 3A to 3D, at least one of each at least one portion, such as a lower portion 211, an upper portion 212, and opposing side portions 213A and 213B, and the tongue portion 214 is configured to be closed together in relation to another at least one portion, such as a lower portion 211, an upper portion 212, and opposing side portions 213A and 213B. The tongue portion 214 is optionally configured to overlap and engage the opposing side portions 213 by way of an overlapping lip structure 215 for eliminating any gaps between each at least one radio-frequency coil 520 (see e.g., FIGS. 5A to 5B) and ensuring decoupling of each at least one radio-frequency coil 520 (see e.g., FIGS. 5A to 5B) in the closed position, whereby a scanning volume, such as a substantially circular scanning, is provided (see e.g., FIG. 7.). Each at least one portion, such as a lower portion 211, an upper portion 212, and opposing side portions 213A and 213B, is optionally configured to articulate in relation to another portion (such as for adjusting size and shape to provide a best fit for a given head, and for facilitating closing of the housing 210) by way of at least one of a hinge, a pin, a ball joint, and a slider. Further, each at least one sub-portion, e.g., of the lower portion 211, the upper portion 212, the opposing side portions 213A and 213B, and even the tongue portion 214, is optionally configured to articulate in relation to another sub-portion (not shown) by way of at least one of a hinge, a pin, a ball joint, and a slider. In particular, FIG. 3A represents a perspective view, FIG. 3B is a bottom view, FIG. 3C is a top view, while FIG. 3D is a side view.

Figure 4A:
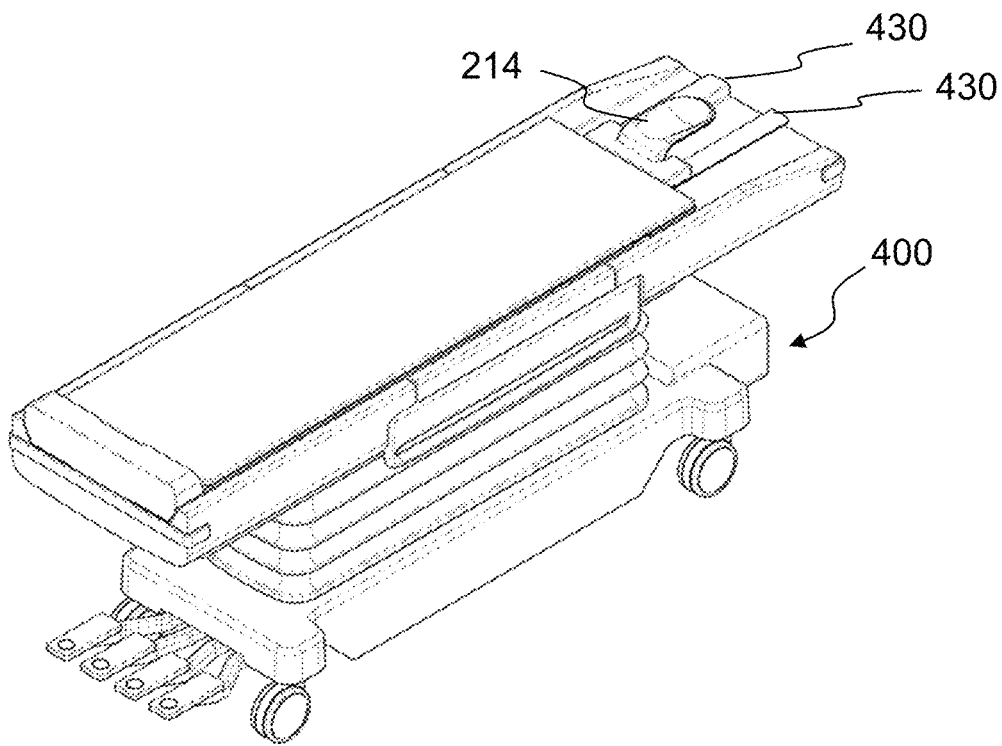
FIG. 4A to 4B respectively illustrates a perspective view and a side view of a transporter, such as an MRI table, for use with a head coil system for enhancing and/or optimizing MRI, as shown in FIGS. 2A to 3D, in accordance with an example of the present disclosure.
Figure 4B:
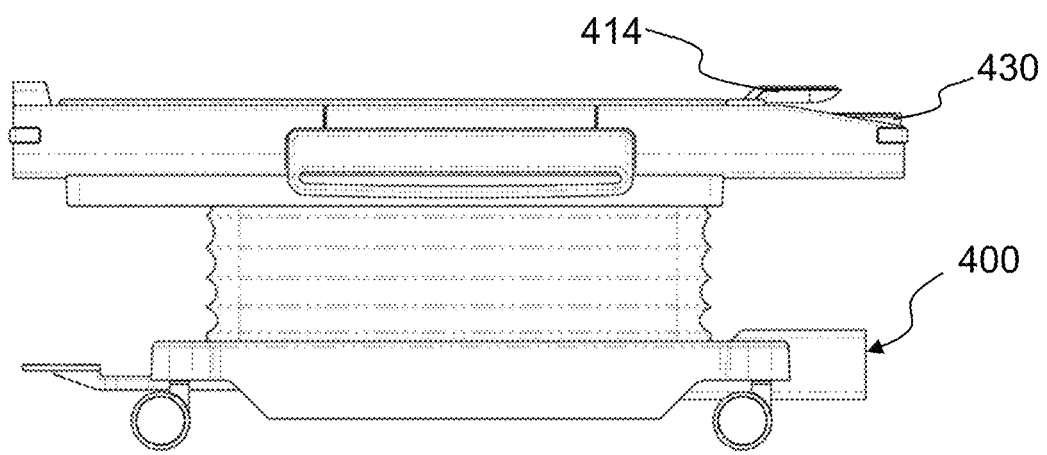

Referring to FIG. 4A to 4B, this diagram illustrates a transporter 400, such as an MRI table, for use with a head coil system 200 for enhancing and/or optimizing MRI, as shown in FIGS. 2A to 3D, in accordance with an embodiment of the present disclosure. The head coil system 200 is adjustable and includes at least one of: at least one guide (not shown) configured to engage at least one corresponding rail 430 of the transporter 400 and to align the tongue portion 214 with the lower portion 211 and the opposing side portions 213A and 213B; and at least one rail (not shown) configured to engage at least one corresponding guide (not shown) of the transporter 400 and to align the tongue portion 214 with the lower portion 211 and the opposing side portions 213A and 213B (see also FIGS. 6A to 6D). FIG. 4A is a perspective view while FIG. 4B is a side view.

Figure 5A:
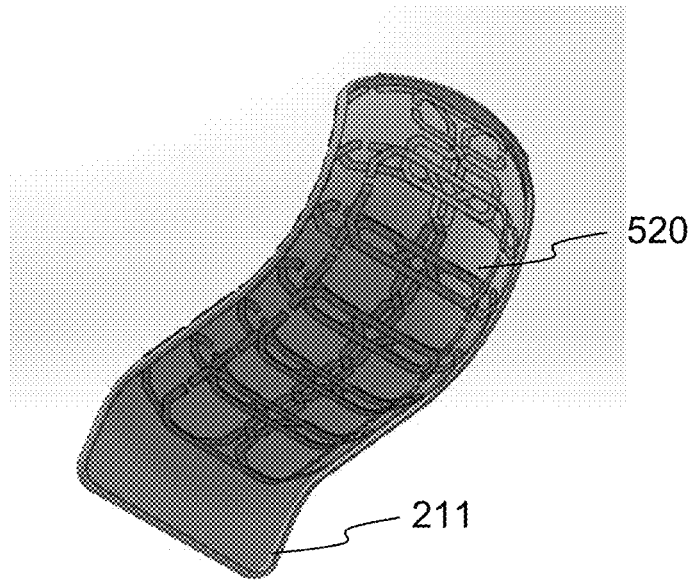
FIGS. 5A to 5B respectively illustrates a perspective view of a lower portion of a head coil system for enhancing and/or optimizing MRI, as shown in FIGS. 2A to 3D, the lower portion optionally comprising radio-frequency coils, in accordance with an example of the present disclosure.
Figure 5B:
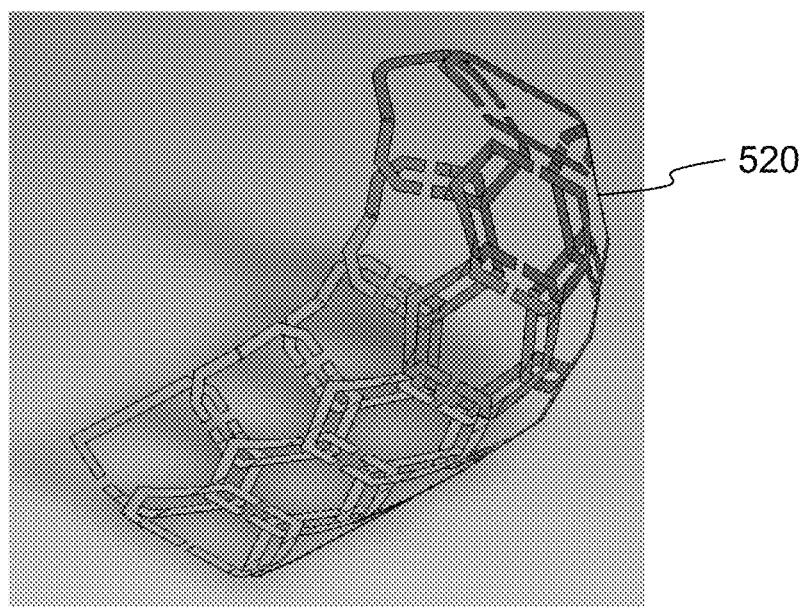
Figure 6A:
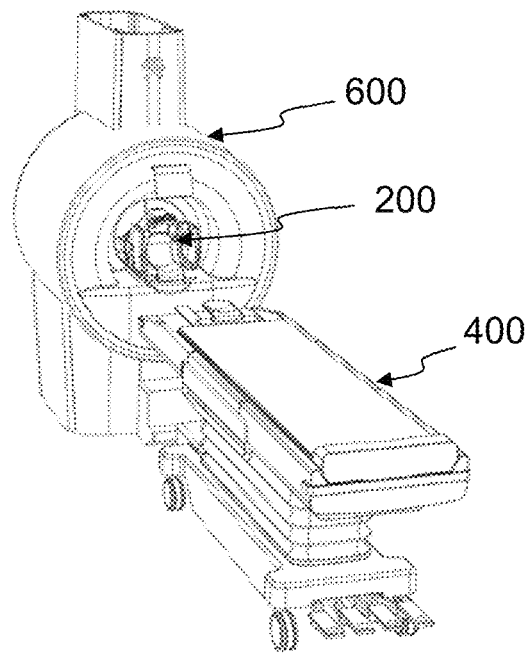
FIGS. 6A to 6D respectively illustrates a perspective view of a head coil system, as shown in FIGS. 2A to 3D, for use with an MRI system, in accordance with an example of the present disclosure.
Figure 6B:
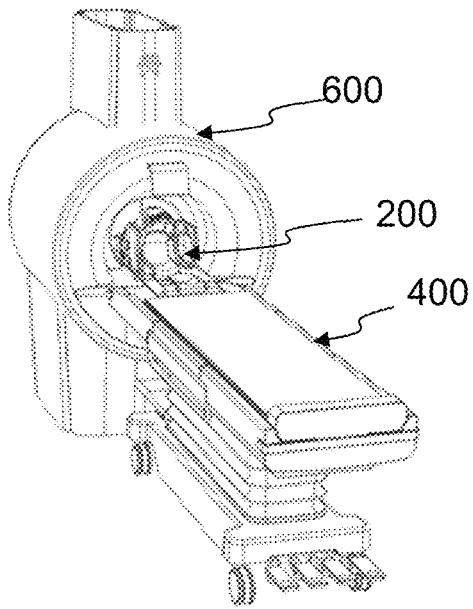
Figure 6C:
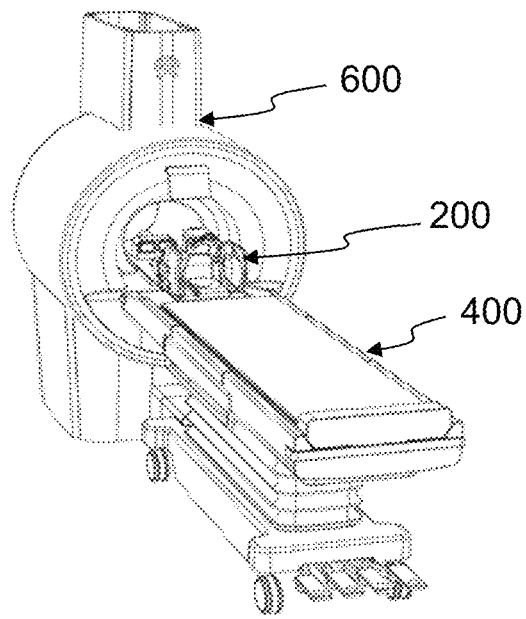
Figure 6D:
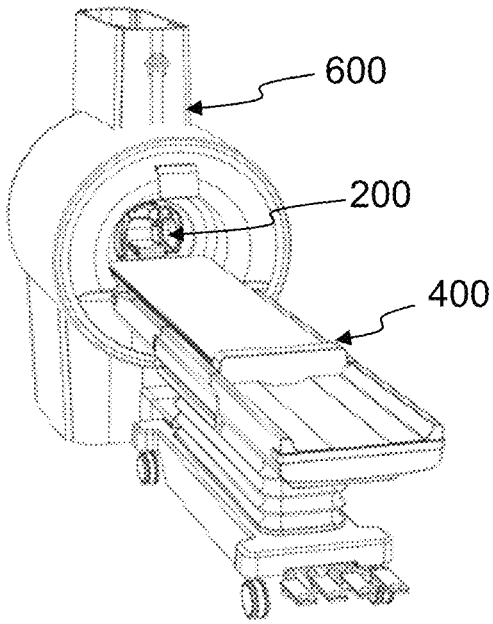

Referring to FIGS. 5A to 5B, this diagrams illustrate perspective views of a lower portion 211 of a head coil system 200 for enhancing and/or optimizing MRI, as shown in FIGS. 2A to 3D, the lower portion 211 including radio-frequency coils 520, in accordance with an example of the present disclosure. The head coil system 200 is adjustable. In some configurations, radio-frequency coils 520 have an overlapping configuration. Array elements in the moveable coil design are conformed to the contours of a sliding assembly. These contoured traces do not reach critical overlap nor are these traces aligned perfectly perpendicular to one another such that the orthogonal magnetic field lines would yield zero coupling. At the furthest extent of the moving coil assembly, isolating array elements from one-another becomes very challenging due to the radial distance between elements. This radial distance exceeds what can be appreciably used for the insertion of decoupling circuits or other conventional methods for isolating RF array elements from one-another.

Figure 8A:
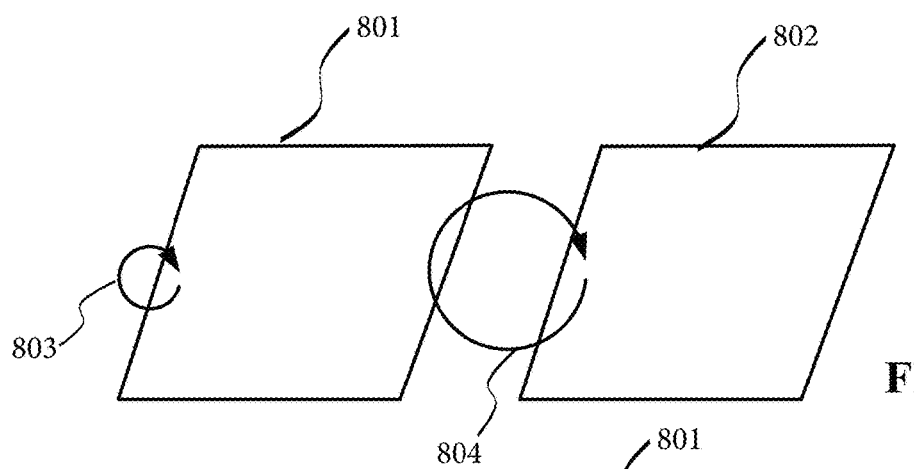
FIG. 8A is a diagram illustrating coupling in a coil pair.

Referring to FIGS. 8A to 8D, the salient features of coil configuration to maintain decoupling are illustrated. FIG. 8A is a diagram illustrating coupling in a coil pair. Elements 801 and 802 represent individual coils. In the illustration, elements 801 and 802 are co-planar. For example, element 801, configured as a loop, according to Faraday's law on induction, emanates magnetic field on each side, as illustrated by circle 803. The magnetic field, generated by induction from element 802, exhibits similar characteristics. As such, the co-planar configuration gives rise to mutual coupling between the two elements, as illustrated by circle 804. Such coupling is predicated on the alignment of magnetic flux from both elements. This mutual coupling can be detrimental for obtaining MR signals.

Figure 8B:
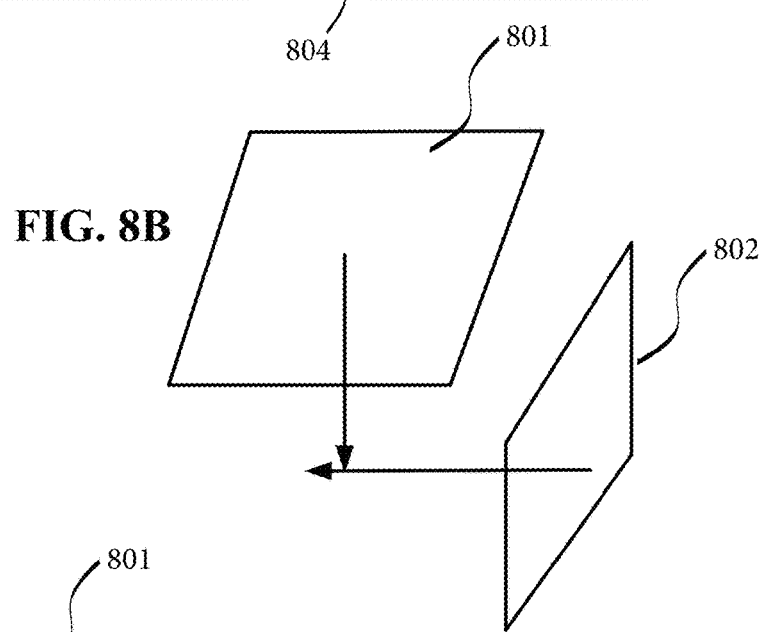
FIG. 8B is a diagram illustrating the coil pair in orthogonal configuration.

Referring to FIG. 8B, a diagram of the coil pair in non-coplanar configuration is illustrated. As demonstrated in FIG. 8A, coupling is proportional to the magnitude of magnetic flux penetrating the internal diameter of a simple loop. When the elements are perpendicularly aligned, as shown in FIG. 8, the magnetic flux vectors of elements 801 and 802 do not pass through each other. In such a case, coupling would be minimized.

Figure 8C:
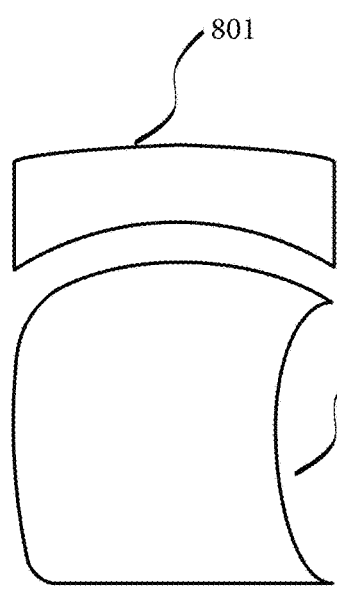
FIG. 8C is diagram illustrating the coupling the coil pair configured as illustrated in FIG. 8B.

However, as illustrated by FIG. 8C, when conforming the perpendicular loops (e.g., to a curved surface, or to transition from one configuration to another configuration), the loop elements (e.g., 801 and 802) may no longer be strictly perpendicular, and a portion of the magnetic flux may penetrate either loop, giving rise to coupling.

Figure 8D:
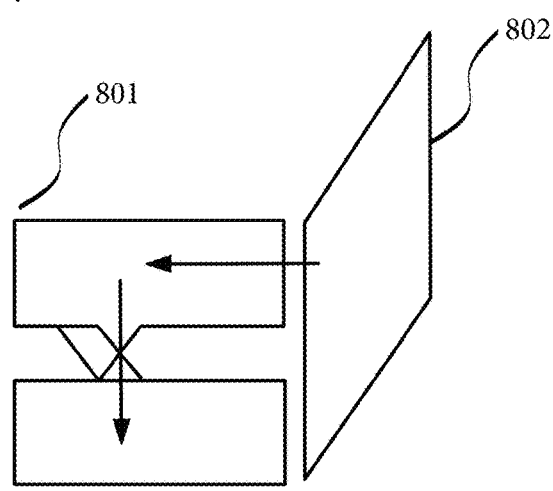
FIG. 8D is diagram illustrating the coil pair with one element as a loop butterfly.

In some examples, element 801 may be configured as a butterfly loop while 802 may be configured as a loop (or vice versa), as illustrated in FIG. 8D. Here, both elements can be incorporated into an RF array for signal detection or reception. However, unlike the case in which the two loop-elements are located next to one another, loop and butterfly elements are innately decoupled due to the orientation of the magnetic field produced by each. As such, for sliding sections as highlighted in FIGS. 2A to 3D, when aligning 'loop-butterfly' pairs along the edges of the individual sliding panels in the RF coil can maintain a decoupled configuration (or a minimized coupling status) across a spectrum of radial distances and modest curvatures.

In MR imaging, RF coils are predominately built and optimized for specific imaging targets. By example, when imaging human subjects, different RF coils are used for head imaging and cardiac imaging, etc. Regardless of the imaging subject, RF arrays generally are prone a common electromagnetic phenomenon—electromagnetic coupling. As illustrated above in FIG. 8A, coupling is a quantification of the level of interference arising between antennae. Coupling degrades array efficiency and SNR, possibly rendering images unsuitable for clinical practice. Therefore, RF coils can be built on fixed, rigid assemblies such that coupling can be mitigated using critical element overlap and low-input impedance preamplifiers. The construction of RF coils on rigid assemblies presents a problem for maximizing array efficiency and SNR as both quantities scale quadratically with proximity to the sample under study. Therefore, with the assembly's design requiring accommodation for the largest variances in human anatomy, maximization of transmission efficiency and maximization of signal-to-noise ratio (SNR) may not be achieved at the same time.

In some instances, moving RF receive array may be developed to overcome these industrial design challenges. This approach may overcome the problems attributed to building an RF coil that is generally over-sized for the majority of the patient population. However, maintaining critical overlap in approach design to reduce coupling may not be possible and there is a consequent degradation in SNR.

In contrast, examples of the present disclosure provide systems and methods for electromagnetically isolating the individual moving parts of the RF array from one another, thereby maintaining a reduced or minimized coupling in the array.

Referring to FIG. 6A to 6D, this diagrams illustrate, in perspective views, a head coil system 200, as shown in FIGS. 2A to 4B, for use with an MRI system. The head coil system 200 is adjustable and includes upper and lower portions 212, 211, opposing side portions 213A and 213B, and a tongue portion 214, the tongue portion 214 engageable with the lower portion 211 and the opposing side portions 213A and 123B, the tongue portion 214 capable of coupling with a transporter 400, wherein the upper and lower portions 212, 211 and the opposing side portions 213 are storable in relation to the MRI system, and wherein the tongue portion 214 is disengaged from the lower portion 211 and the opposing side portions 213A and 213B, such as when the system 200 is not in use, in accordance with an example of the present disclosure.

Still referring to FIG. 6A to 6D, by using the head coil system 200, which is adjustable, a patient's head is comfortably disposed on the tongue portion 214, wherein fine adjustments may be made to any sub-portions thereof before the patient's head enters the housing 210. The transporter 400 can be moved toward the MRI system, wherein the tongue portion 214 readily engages and/or registers with the lower portion 211 and the opposing side portions 213A and 213B by way of at least one guide and at least one rail. When registered, if using an adjustable embodiment of the system 200, medical personnel, such as an MRI technician may adjust the upper portion 212 in relation to the opposing portions 213A and 213B and may adjust the opposing portions 213A and 213B in relation to at least one of the lower portion 211 and the tongue portion 214 by way of articulation, disposition, and engagement. Further, fine adjustments may be made by way of articulation, disposition, and engagement of any sub-portions thereof.

In these illustrations, the upper and lower portions 212, 211 and the opposing side portions 213A and 213B are slidable in relation to the MRI system, and the tongue portion 214 can be engaged with the lower portion 211 and the opposing side portions 213, such as by rolling the transporter 400 toward the MRI system, in accordance with an embodiment of the present disclosure.

In these illustrations, the tongue portion 214 can be engaged with the lower portion 211 and the opposing side portions 213A and 213B, by rolling the transporter 400 toward the MRI system and by sliding the upper and lower portions 212, 211 and the opposing side portions 213A and 213B outward from the MRI system until the tongue portion 214 is fully engaged with the lower portion 211 and the opposing side portions 213A and 213B, in accordance with an example of the present disclosure.

In these illustrations, the tongue portion 214 can be fully engaged with the lower portion 211 and the opposing side portions 213A and 213B, such as by rolling the transporter 400 toward the MRI system until the tongue portion 214 is fully engaged with the lower portion 211 and the opposing side portions 213A/213B and continuing to roll the transporter 400 toward the MRI system until the system 200 is fully disposed within the MRI system, according to an example of the present disclosure.

As illustrated, the housing of the head coil system 200 may be adjustable or, alternatively, fixed or integrally formed, wherein the housing is storable in the MRI system and deployable therefrom for use. In some embodiments of the present disclosure, the transporter 400 includes an MRI table and thus obviating a need for a stretcher. As such, an emergency patient can be more rapidly imaged in order to accelerate diagnosis and therapy. The housing of the fixed head coil system is accommodated by an MRI system, e.g., by sliding the housing into the MRI system when the housing in not in use, and for deployment of the housing of the fixed head coil system by sliding the housing from the MRI system for use. In the fixed head coil system, the tongue portion 214 is lockable with the lower portion 211 by moving the transporter 400 to the MRI system, thereby efficiently disposing the fixed head coil system in relation to a head of a patient, and thereby efficiently readying the head of the patient for imaging. In the fixed head coil system, the tongue portion 214 is undockable from the lower portion 211 by moving the transporter 400 from the MRI system, thereby efficiently readying the patient for therapy.

Figure 7:
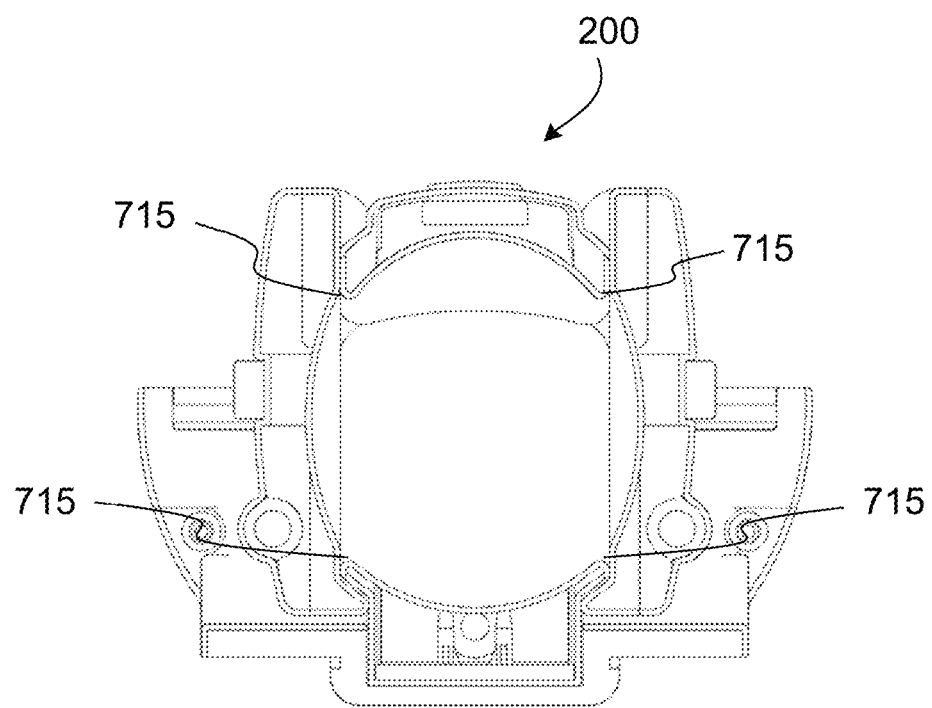
FIG. 7 is a diagram illustrating a section view of a head coil system for enhancing and/or optimizing MRI in a closed position, wherein at least one overlapping portion, such as at least one overlapping lip, forms a cavity, such as a substantially circular scanning surface or scanning bore, in accordance with an example of the present disclosure.

FIG. 7 is a diagram illustrating a section view of a head coil system for enhancing and/or optimizing MRI in a closed position, wherein at least one overlapping portion, such as at least one overlapping lip, forms a cavity, such as a substantially circular scanning surface or scanning bore, in accordance with an example of the present disclosure. The head coil system 200 is adjustable. At least one of the upper portion 212, the lower portion 211, and the tongue portion 214 is configured to overlap and engage the opposing side portions 213A and 213B by way of an overlapping lip structure 715 for eliminating any gaps between each at least one radio-frequency coil 520 and ensuring decoupling of each at least one radio-frequency coil 520 in the closed position, whereby a scanning volume, such as a substantially circular scanning, is provided.

Radio frequency (RF) arrays are a subsystem of a magnetic resonance imaging (MRI) scanner responsible for performing excitation, receiving signals or a combination of both functions. Arrays designed for signal excitation are known as "transmit coils." Arrays designed for signal reception are known as "receive coils." Arrays designed for both functions are known as "transceive coils." Generally, RF arrays are composed of multiple resonating antennae that are disposed in a judicious manner about the imaging region such that: (i) efficiency is maximized during transmission, ii) the magnitude of the received signal is maximized during reception (signal-to-noise ratio or 'SNR'), and (iii) a combination of both.

Examples disclosed in the present disclosure judiciously achieve de-coupling status in, for example, a transmit array that is conformable. The decoupling, or minimized coupling, can be maintained when the transmit array is reconfigured to change from one configuration to another configuration, without compromising the above objectives.

While in some instances, loop-butterfly pairs are employed specifically for decoupling for co-planar loops in an array, examples disclosed in the present disclosure speak to using loop-butterfly pair and loop pair in non-coplanar configurations. Electromagnetically, this change in orientation (from co-planar to non-coplanar) represents a fundamentally different mechanism when using loop-butterfly pairs on a conformal, sliding coil assembly with butterfly-loop pairs disposed along all three cartesian axes.

Additionally, coplanar loop-butterfly decoupling provides a distinctly different method of image acquisition. For example, loop-butterfly pairs may be used quadrature pairs to combine signals through analog filters. Yet, examples of the present invention do not require signal combination through analog filters. In fact, MR signals received in a coil system example as disclosed herein can be digitally recombined in a more sophisticated image reconstruction algorithm using specialized digital signal processing techniques. In some instances, the head coil assembly receives, in response to one or more radio frequency (RF) excitation pulses directed at the subject's head placed inside the head coil assembly, first MR signals at the first element of the decoupling pair and second MR signals at the second decoupling pair. In these instances, the first MR signals and the second MR signals may not maintain a fixed phase shift, as exhibited when the first MR signals and the second MR signals are in-phase and quadrature signals.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A head coil assembly operable to perform magnetic resonance (MR) imaging of a subject's head, comprising:
a housing comprising a lower portion, an upper portion, a left portion, and a right portion,
wherein each portion comprises two or more radio-frequency (RF) coils operable to perform magnetic resonance (MR) imaging of the subject's head placed inside the housing,
wherein the portions are sized and shaped to adjustably conform to a curvature of the subject's head such that the portions are operable to transition from an open position to a closed position,
wherein when the portions are in the open position, the portions are sufficiently apart from each other to accommodate the subject's head being slid into the housing,
wherein when the portions are in the closed position, the portions are adjusted to tighten a wrap around the subject's head along the curvature,
wherein the two or more RF coils in each portion are disposed in such manner that when the portions are operated to transition from the open position to the closed position, the RF coils of each portion remain decoupled to each other even along edges of each portion,
wherein the housing further comprises butterfly-loop decoupling pairs disposed along edges of each individual portion, wherein each butterfly-loop decoupling pair comprises a loop element and a butterfly element, wherein the loop element is located on a first portion while the butterfly element is located on a second portion, wherein the first portion and the second portion are neighboring portions from among the lower portion, the upper portion, the left portion, and the right portion,
wherein each butterfly-loop decoupling pair is configured to receive, in response to one or more radio frequency (RF) excitation pulses directed at the subject's head placed inside the head coil assembly, first MR signals at the loop element and second MR signals at the butterfly element.

2. The head coil assembly of claim 1, further comprising:
a tongue sized and shaped to hold the subject's head when the subject is lying on a transporter, the tongue dockable with the lower portion to slide the subject's head into the housing when the housing is in the open position.

3. The head coil assembly of claim 1, wherein each butterfly-loop decoupling pair is not configured as a quadrature pair such that the first MR signals received at the loop element and the second MR signals received at the butterfly element maintain no fixed phase shift, and wherein the first and second MR signals are digitized and then digitally recombined when an MR image is reconstructed.

4. The head coil assembly of claim 1, wherein the first MR signals received at the loop element and the second MR signals received at the butterfly element are analog signals and combined after digitization.

5. The head coil assembly of claim 1, wherein the housing comprises loop-loop decoupling pairs disposed along edges of each individual portion.

6. The head coil assembly of claim 5, wherein each loop-loop decoupling pair comprises a first loop element located on a first portion and a second loop element located on a second portion, wherein the first portion and the second portion are neighboring portions from among the lower portion, the upper portion, the left portion, and the right portion, and wherein the loop-loop decoupling pair remains orthogonally disposed when the portions transition from the open position to the closed position or vice versa.

7. The head coil assembly of claim 6, wherein each loop-loop decoupling pair is configured to receive, in response to one or more radio frequency (RF) excitation pulses directed at the subject's head placed inside the head coil assembly, first MR signals received at the loop element and second MR signals received at the butterfly element, and wherein the first and second MR signals are digitized and then digitally recombined when an MR image is reconstructed.

8. The head coil assembly of claim 7, wherein each loop-loop decoupling pair is configured such that the first MR signals received at the first loop element and the second MR signals received at the second loop element are not fixed in phase shifts relative to each other.

9. A method for operating a head coil assembly on a magnetic resonance imaging (MRI) system, the method comprising:
configuring a housing of the head coil assembly in an open position,
wherein the housing comprises a lower portion, an upper portion, a left portion, a right portion, and a tongue, wherein each portion comprises two or more radio-frequency (RF) coils, wherein the RF coils of each portion are decoupled to coils from other portions, wherein each portion is sized and shaped to adjustably conform to a curvature of a subject's head,
wherein the housing further comprises butterfly-loop decoupling pairs disposed along edges of each individual portion, and wherein the butterfly-loop decoupling pair comprises a loop element and a butterfly element;
docking the tongue with the lower portion by moving a transporter carrying the subject's head to the MRI system;
reconfiguring the housing of the head coil assembly from the open position wherein the portions are sufficiently apart from each other to accommodate the subject's head being slid into the housing to a closed position wherein the portions are adjusted to tighten a wrap around the subject's head along the curvature, wherein the RF coils of each portion remain decoupled to RF coils from other portions even along edges of each portion; and
sliding the housing into the MRI system; and
operating the MRI system to receive, in response to one or more radio frequency (RF) excitation pulses directed at the subject's head placed inside the head coil assembly, first MR signals at the loop element and second MR signals at the butterfly element.

10. The method of claim 9, wherein the first MR signals received at the loop element and the second MR signals received at the butterfly element maintain no fixed phase shift, and wherein the first and second MR signals are digitized and then digitally recombined when an MR image is reconstructed.

11. The method of claim 9, wherein the first MR signals received at the loop element and the second MR signals received at the butterfly element are analog signals and combined after digitization.

12. The method of claim 9, wherein the housing comprises loop-loop decoupling pairs disposed along edges of each individual portion, and wherein each loop-loop decoupling pair comprises a first loop element and a second loop element.

13. The method of claim 12, wherein each loop-loop decoupling pair comprises a first loop element located on a first portion and a second loop element located on a second portion, wherein the first portion and the second portion are neighboring portions from among the lower portion, the upper portion, the left portion, and the right portion, and wherein the loop-loop decoupling pair remains orthogonally disposed when the portions transition from the open position to the closed position or vice versa.

14. The method claim 13, further comprising:
operating the MRI system to receive, in response to one or more radio frequency (RF) excitation pulses directed at the subject's head placed inside the head coil assembly, receive first MR signals at the first loop element and second MR signals at the second loop element, and wherein the first and second MR signals are digitized and then digitally recombined when an MR image is reconstructed.

15. The method of claim 14, wherein the first MR signals received at the first loop element and the second MR signals received at the second loop element are not fixed in phase shifts relative to each other.

\* \* \* \* \*